(12) United States Patent
Bogert

(10) Patent No.: US 10,449,067 B2
(45) Date of Patent: Oct. 22, 2019

(54) LOCKED SEGMENTS PUSHABLE STENT-GRAFT

(71) Applicant: C. R. Bard, Inc., Tempe, AZ (US)

(72) Inventor: David L. Bogert, Tempe, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 139 days.

(21) Appl. No.: 15/228,871

(22) Filed: Aug. 4, 2016

(65) Prior Publication Data

US 2016/0338861 A1    Nov. 24, 2016

Related U.S. Application Data

(62) Division of application No. 12/666,031, filed as application No. PCT/US2008/067620 on Jun. 20, 2008, now Pat. No. 9,427,343.

(60) Provisional application No. 60/936,889, filed on Jun. 22, 2007.

(51) Int. Cl.
| | |
|---|---|
| *A61F 2/89* | (2013.01) |
| *A61F 2/07* | (2013.01) |
| *A61F 2/915* | (2013.01) |
| *A61F 2/90* | (2013.01) |

(52) U.S. Cl.
CPC ............. *A61F 2/89* (2013.01); *A61F 2/07* (2013.01); *A61F 2/90* (2013.01); *A61F 2/915* (2013.01); *A61F 2002/072* (2013.01); *A61F 2002/075* (2013.01); *A61F 2002/91591* (2013.01); *A61F 2220/005* (2013.01); *A61F 2220/0075* (2013.01); *A61F 2230/0013* (2013.01); *A61F 2230/0054* (2013.01); *A61F 2230/0056* (2013.01)

(58) Field of Classification Search
CPC .......... A61F 2002/072; A61F 2002/075; A61F 2002/9155; A61F 2002/91591; A61F 2/07; A61F 2/86; A61F 2/89; A61F 2/90; A61F 2/915

See application file for complete search history.

(56) References Cited

U.S. PATENT DOCUMENTS

| | | | |
|---|---|---|---|
| 4,955,899 | A | 9/1990 | Della Corna et al. |
| 5,591,197 | A | 1/1997 | Orth et al. |
| 5,667,523 | A | 9/1997 | Bynon et al. |
| 5,824,040 | A | 10/1998 | Cox et al. |
| 5,970,880 | A | 10/1999 | Perotto |

(Continued)

FOREIGN PATENT DOCUMENTS

| | | |
|---|---|---|
| JP | 11-501243 | 2/1999 |
| JP | 2001-526080 A | 12/2001 |

(Continued)

OTHER PUBLICATIONS

JP 2010-513436 filed Dec. 22, 2009 Office Action dated Jan. 11, 2013.

(Continued)

*Primary Examiner* — Sarah A Simpson
(74) *Attorney, Agent, or Firm* — Rutan & Tucker, LLP

(57) ABSTRACT

An implantable prosthesis includes a scaffold with a plurality of expandable segments axially spaced apart along a substrate, adjacent segments connected by one or more support members when the prosthesis is in a collapsed configuration and disconnected when the prosthesis is in an expanded configuration.

13 Claims, 5 Drawing Sheets

(56) References Cited

U.S. PATENT DOCUMENTS

| | | |
|---|---|---|
| 6,042,605 A | 3/2000 | Martin et al. |
| 6,110,198 A * | 8/2000 | Fogarty .................... A61F 2/07 128/898 |
| 6,124,523 A | 9/2000 | Banas et al. |
| 6,264,684 B1 | 7/2001 | Banas et al. |
| 6,270,524 B1 | 8/2001 | Kim |
| 6,312,458 B1 | 11/2001 | Golds |
| 6,361,637 B2 | 3/2002 | Martin et al. |
| 6,398,803 B1 | 6/2002 | Layne et al. |
| 6,494,904 B1 | 12/2002 | Love |
| 6,520,986 B2 | 2/2003 | Martin et al. |
| 6,558,414 B2 | 5/2003 | Layne |
| 6,652,570 B2 | 11/2003 | Smith et al. |
| 6,673,103 B1 | 1/2004 | Golds et al. |
| 6,695,833 B1 | 2/2004 | Frantzen |
| 6,712,844 B2 | 3/2004 | Pacetti |
| 6,770,087 B2 | 8/2004 | Layne et al. |
| 6,881,221 B2 | 4/2005 | Golds |
| 6,911,040 B2 | 6/2005 | Johnson et al. |
| 6,945,991 B1 | 9/2005 | Brodeur et al. |
| 7,094,255 B2 | 8/2006 | Penn et al. |
| 7,122,052 B2 | 10/2006 | Greenhalgh |
| 7,147,660 B2 | 12/2006 | Chobotov et al. |
| 7,169,175 B2 | 1/2007 | Cottone, Jr. et al. |
| 7,351,255 B2 | 4/2008 | Andreas |
| 8,313,524 B2 | 11/2012 | Edwin et al. |
| 9,427,343 B2 | 8/2016 | Bogert |
| 2003/0229390 A1 | 12/2003 | Ashton et al. |
| 2004/0024443 A1 | 2/2004 | Dwyer et al. |
| 2004/0167609 A1 | 8/2004 | Majercak |
| 2004/0230288 A1 | 11/2004 | Rosenthal |
| 2005/0085896 A1 * | 4/2005 | Bonsignore ............... A61F 2/91 623/1.15 |
| 2005/0278017 A1 | 12/2005 | Gregorich |
| 2006/0069424 A1 | 3/2006 | Acosta et al. |
| 2006/0195175 A1 | 8/2006 | Bregulla |
| 2008/0027534 A1 | 1/2008 | Edwin et al. |
| 2010/0324657 A1 | 12/2010 | Bogert |

FOREIGN PATENT DOCUMENTS

| | | |
|---|---|---|
| JP | 2006-61718 | 3/2006 |
| JP | 2006-512099 A | 4/2006 |
| WO | 1995029647 A2 | 11/1995 |
| WO | 1997017039 A1 | 5/1997 |
| WO | 1998037833 A1 | 9/1998 |
| WO | 2001001887 A1 | 1/2001 |
| WO | 2005122960 A2 | 12/2005 |
| WO | 2006026725 A2 | 3/2006 |

OTHER PUBLICATIONS

PCT/US2008/067620 filed Jun. 20, 2008 International Preliminary Report on Patentability dated Dec. 22, 2009.

PCT/US2008/067620 filed Jun. 20, 2008 International Search Report dated Dec. 29, 2008.

PCT/US2008/067620 filed Jun. 20, 2008 Written Opinion dated Dec. 29, 2008.

PCT/US2008/067630 filed Jun. 20, 2008 International Preliminary Report on Patentability dated Dec. 22, 2009.

PCT/US2008/067630 filed Jun. 20, 2008 International Search Report dated Jan. 16, 2009.

PCT/US2008/067630 filed Jun. 20, 2008 Written Opinion dated Jan. 16, 2009.

U.S. Appl. No. 12/666,031, filed Dec. 22, 2009 Advisory Action dated Mar. 27, 2014.

U.S. Appl. No. 12/666,031, filed Dec. 22, 2009 Final Office Action dated Dec. 9, 2013.

U.S. Appl. No. 12/666,031, filed Dec. 22, 2009 Non-Final Office Action dated Jul. 24, 2012.

U.S. Appl. No. 12/666,158, filed Sep. 17, 2010 Advisory Action dated Nov. 2, 2012.

U.S. Appl. No. 12/666,158, filed Sep. 17, 2010 Examiner's Answer dated Jun. 10, 2013.

U.S. Appl. No. 12/666,158, filed Sep. 17, 2010 Final Office Action dated Aug. 17, 2012.

U.S. Appl. No. 12/666,158, filed Sep. 17, 2010 Non-Final Office Action dated Oct. 13, 2011.

* cited by examiner

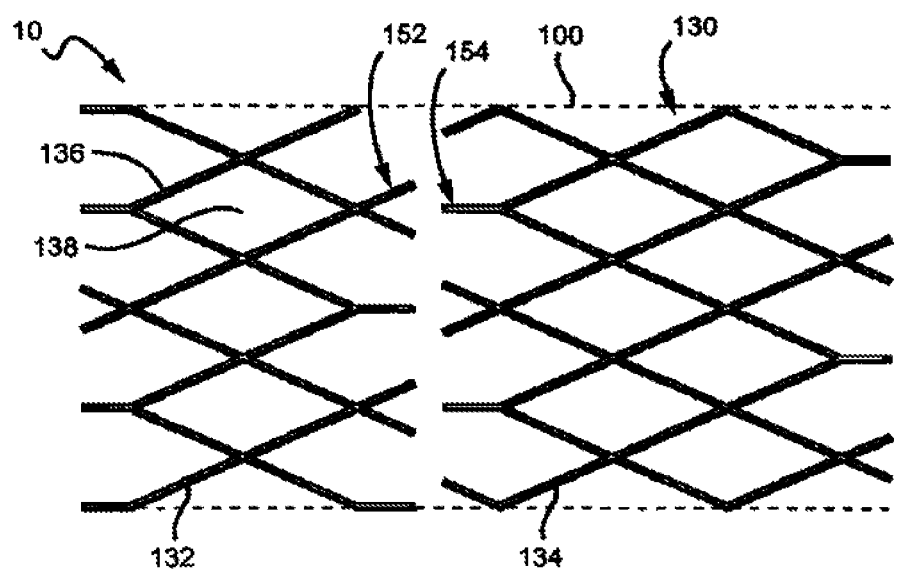

LOCKED SEGMENTS PUSHABLE STENT-GRAFT

PRIORITY

This application is a division of U.S. patent Ser. No. 12/666,031, filed on Dec. 22, 2009, now U.S. Pat. No. 9,427,343, which is a U.S. national stage under 35 U.S.C. § 371 of International Application No. PCT/US2008/067620, filed Jun. 20, 2008, which claims priority to U.S. Provisional Application No. 60/936,889, filed on Jun. 22, 2007, each of which applications is incorporated herein by reference in its entirety.

BACKGROUND

Intraluminal prostheses used to maintain, open, or dilate blood vessels are commonly known as stents. Stent constructions generally include lattice type cylindrical frames that define a plurality of openings. Common framework for stents include, for example, individual rings linked along the length of the stent by a linking member, a continuous helically wrapped member (that may include one or more linking members), a braid or a mesh formed into a tubular structure, and a series of interconnected struts. Stents may be formed by arranging one or more members in a pattern along a longitudinal axis to define essentially a cylinder and connecting the one or more members or otherwise affixing them in position (e.g., interconnecting with a filament). Stents may also be formed by cutting openings into a tube of material (e.g., shape memory).

Stents may have self-expanding and/or balloon expandable properties. Self-expanding stents are delivered to a blood vessel in a collapsed condition and expand in vivo following the removal of a constraining force and/or in the presence of an elevated temperature (due to material properties thereof), whereas balloon expandable stents are generally crimped onto a balloon catheter for delivery and require the outwardly directed force of a balloon for expansion. Stents can be made of various metals and polymers and can include a combination of self-expanding and balloon expandable properties.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts formed of ePTFE include a microstructure characterized by spaced apart nodes connected by fibrils, the distance between the nodes defined as internodal distance (IND), and are generally extruded either as a tube or as a sheet or film that is fashioned into a tube. Grafts can also be created from fibers woven or knitted into a generally tubular shape.

It is known in the art to use stents in combination with vascular grafts to form stent grafts. Because stent-grafts are often intraluminally deployed in vessels of varying sizes and tortuosity, flexibility can be an important consideration. Flexibility can be imparted to a stent-graft in a variety of ways, including, for example, connection of the stent to the one or more graft layers, configuration of the stent and/or graft layer(s), spacing of the stent struts, rings, or members along the length of the graft(s), etc. For example, U.S. Pat. Nos. 6,398,803 and 6,770,087 to Layne et al., which are incorporated by reference in their entirety into this application, describe a graft layer with openings to enhance flexibility. U.S. Pat. No. 6,558,414 to Layne, which is incorporated by reference in its entirety into this application, describes another type of graft layer to enhance flexibility.

Another important consideration in the design of a stent-graft is the ability of the stent to withstand stress and fatigue, caused, for example, by plastic deformations occurring at strut junctions when the stent is subjected to circumferential forces. Stent strength can be enhanced through material choice, stent configuration, arrangement and configuration of graft layers, connecting members between stent members, etc. Yet another consideration in the design of a stent-graft is its columnar strength in the compressed configuration to enable the stent-graft to be pushed out of a delivery sheath, for example, without buckling or deforming. This consideration, however, must be balanced with flexibility considerations, such as those discussed above.

The following references relate to stents and stent-grafts: U.S. Pat. No. 5,591,197 to Orth et al.; U.S. Pat. No. 6,695,833 to Frantzen; U.S. Patent Application No. 2003/0229390 to Ashton et al.; and U.S. Patent Application No. 2004/0230288 to Rosenthal, each of which is incorporated by reference in its entirety into this application.

Applicants have recognized that it would be desirable to provide a stent-graft that is relatively stiff in a collapsed configuration and more flexible in a deployed expanded configuration, embodiments of which are described herein along with methods of making same.

BRIEF SUMMARY

Accordingly, stent-grafts are described herein with different columnar strengths in the collapsed and expanded configurations, the columnar strength of the stent-graft in the collapsed configuration greater than the columnar strength of the stent-graft in the expanded configuration.

In one embodiment, an implantable prosthesis having an expanded configuration defining an expanded perimeter and a collapsed configuration defining a collapsed perimeter smaller than the expanded perimeter includes a generally tubular substrate defining a longitudinal axis, a plurality of expandable segments disposed over the substrate and spaced apart along the longitudinal axis, and a plurality of support members connected to the expandable segments and extending transversely therefrom, each support member including a first element connected to a first expandable segment and a second element connected to a second expandable segment adjacent to the first expandable segment, the first element and second element engaged in the collapsed configuration and disengaged in the expanded configuration.

In another embodiment, an implantable prosthesis having an expanded configuration defining an expanded perimeter and a collapsed configuration defining a collapsed perimeter smaller than the expanded perimeter includes a generally tubular substrate defining a longitudinal axis, a scaffold disposed over the substrate, including a plurality of support members positioned generally parallel to the longitudinal axis, each support member including a first element engaged with a second element in the collapsed configuration, at least one of the first and second elements moving to a position generally oblique to the longitudinal axis in the expanded configuration such that the first and second elements are disengaged.

In yet another embodiment, a stent graft exhibits a first columnar strength in a collapsed configuration and a second columnar strength less than the first columnar strength in an expanded configuration, the stent-graft including a plurality of spaced apart support members connecting adjacent expandable segments, each support member including a first element coupled to a second element in the collapsed configuration, the first and second elements uncoupling upon expansion of the stent-graft to the expanded configuration.

In one embodiment, a method of implanting a stent-graft having an expanded configuration defining an expanded perimeter and a collapsed configuration defining a collapsed perimeter smaller than the expanded perimeter includes placing a stent-graft in a delivery device in the collapsed configuration, the stent-graft including a generally tubular substrate defining a longitudinal axis, a scaffold disposed over the substrate, including a plurality of support members positioned generally parallel to the longitudinal axis, each support member including a first element engaged with a second element in the collapsed configuration, delivering the stent-graft to a desired location, and expanding the stent-graft to the expanded configuration, the first element disengaging from the second element.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 1C is a partial side view of another embodiment of an implantable prosthesis in a representative expanded configuration, including a scaffold with expandable segments with the support members disengaged.

FIG. 1D is a partial side view of another embodiment of an implantable prosthesis in a representative expanded configuration, including a scaffold with expandable segments with the support members disengaged.

DESCRIPTION OF THE PREFERRED EMBODIMENTS

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "body," "patient," "host," and "subject" refer to any human or animal subject and are not intended to limit the systems or methods to human use, although use of the subject invention in a human patient represents a preferred embodiment.

Figure 1A:
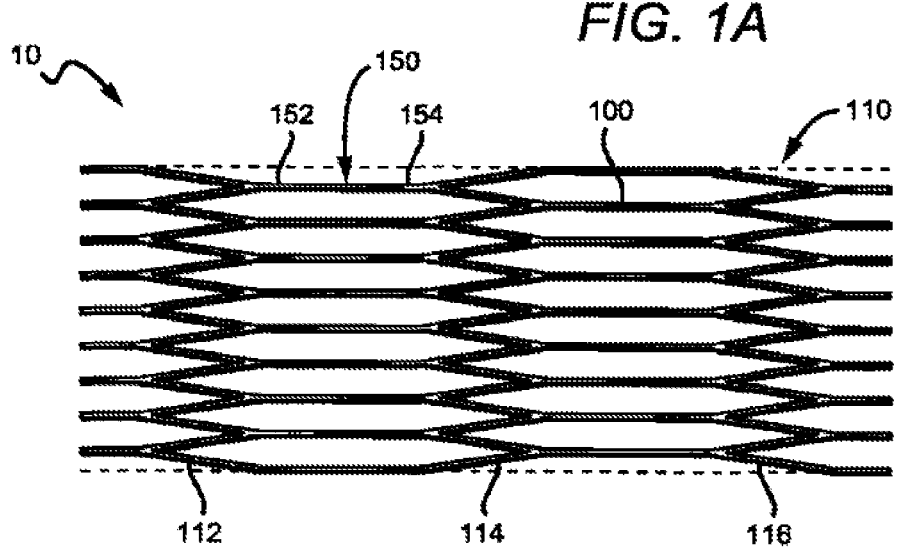
FIG. 1A is a partial side view of one embodiment of an implantable prosthesis to a representative compressed configuration, including expandable segments with support members engaged.
Figure 1B:
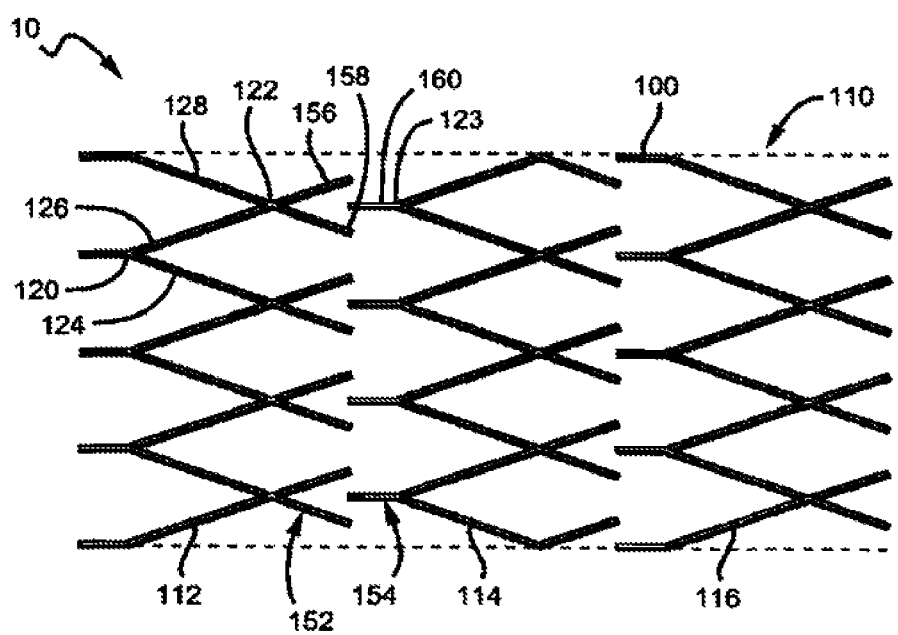
FIG. 1B is a partial side view of the embodiment of FIG. 1A in a representative expanded configuration, including expandable segments with support members disengaged.

Referring now to FIGS. 1A and 1B, a portion of an implantable prosthesis 10, such as a stent-graft, is shown, including a substrate 100, expandable segments 112, 114, 116, and support members 150. The implantable prosthesis is designed to collapse and expand radially in a uniform or non-uniform fashion. FIG. 1A shows the implantable prosthesis 10 in a generally collapsed configuration having a collapsed perimeter. FIG. 1B shows the implantable prosthesis 10 in an expanded configuration that defines an expanded perimeter larger than the collapsed perimeter. The scaffold 110 provides the radial strength of the prosthesis 10 to open a narrowed section of a lumen and maintain that section in an open position to permit blood flow therethrough. The scaffold 110 can be a stent having a stent design, including a segmented stent design, a helical stent design, a solid stent design, or combinations thereof. The scaffold may have self-expanding properties, balloon-inflatable properties, or a combination thereof.

Support members 150 are connected to the scaffold and provide longitudinal stiffness/columnar strength in the collapsed configuration. The support members 150 may be made of the same material as the expandable members and can be either integral (e.g., first and second elements are formed with the expandable members during manufacture thereof) or attached as a separate elements. The support members in this embodiment include two elements 152 and 154. The first element 152 connects to one expandable segment 112, while the second element 154 connects to an adjacent expandable segment 114. The first and second elements 152 and 154 are engaged in the collapsed configuration and are disengaged in the expanded configuration. The term "engaged" as used herein with respect to the various embodiments of first and second elements means at least some contact between the elements, which is generally maintained in the collapsed configuration of the prosthesis. Other terms with the same or similar meaning with respect to the first and second elements include, for example, coupled, connected, attached, etc. In the expanded configuration, the disengagement of support member elements results in a relative decrease in columnar strength for the prosthesis 10 but a relative increase in flexibility and fatigue resistance.

The implantable prosthesis 10 includes a graft or substrate layer 100. This layer in one embodiment is a generally tabular polymer member disposed along the inner surface of the scaffold. The substrate 100 provides a base for the scaffold 100 and provides the prosthesis 10 with a smooth inner surface. The substrate 100 generally defines the longitudinal axis of the implantable prosthesis 10 and may be disposed along the length of the scaffold or only a portion thereof. The substrate 100 has a thickness generally in the range of approximately 10 microns to approximately 200 microns, and preferably in the range of approximately 20 microns to approximately 80 microns. The substrate 100 is flexible and compressible. Potential materials for a substrate include, for example, expanded polytetrafluoroethylene (ePTFE), polyester, polyurethane, fluoropolymers, polytetrafluoroethylene, silicones, urethanes, ultra high molecular weight polyethylene fibers, aramid fibers, and combinations thereof.

One preferred embodiment for a substrate material is ePTFE. The node-fibril microstructure of an ePTFE substrate may include various orientations for the fibrils, but preferably, the fibrils are oriented generally parallel to the longitudinal axis of the substrate. The average internodal distance of the substrate is preferably in the range of approximately 6 microns to approximately 80 microns. The substrate may include a bioactive agent and/or a carbon component along a blood contacting surface thereof. An ePTFE substrate may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc.

The scaffold 110 provides radial strength to support a bodily lumen in an open position to permit blood flow and includes expandable segments 112, 114, 116 positioned along the longitudinal axis of the prosthesis 10, and disposed over an outer surface of the substrate 100. The expandable segments 112, 114, 116 are sufficiently elastic and radially rigid to remain open when inserted into a body lumen and are designed to radially collapse to aid in the delivery of the prosthesis into the body. The expandable segments in one embodiment may be formed of a shape memory material, including, for example, shape memory metals, shape memory alloys, super elastic shape memory metal alloys, linear elastic shape memory alloy, metal alloys, shape memory polymers, polymers, bio-resorbable material, and combinations thereof. One preferred shape memory material is Nitinol, while another is a cobalt chrome alloy. The sections may also be formed of metal, such as, for example, stainless steel, platinum, and Elgiloy, or certain polymers.

It should also be noted that one or more expandable segments and/or support members of the scaffold may be made of a bio-resorbable material. As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above. Potential materials for the prosthesis described herein include, for example, biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes.

The scaffold may be connected to the substrate by various methods, which can be facilitated by the material selection for the scaffold, substrate and/or coatings, if utilized. An adhesive, a polymer bonded by a solvent, sutures, or other methods may be used to connect the scaffold to the substrate. Other alternatives known in the art are additionally within the scope of this invention, including weaving the substrate around the scaffold. The substrate may additionally be longitudinally compressed before attaching to the scaffold. The substrate is compressed from a first length to a second length, which is approximately 50% to 97% of the first length. Longitudinal compression of an ePTFE graft is described in U.S. Pat. No. 4,955,899 to Della Corna et al. and is incorporated by reference in its entirety in this application.

In one embodiment, an adhesive may be disposed between the scaffold and the substrate to bond the scaffold to the substrate at the interface between the expandable segments and the substrate. Suitable biocompatible bonding agents may include polytetrafluoroethylene, polyurethane, polyethylene, polypropylene, polyamides, polyimides, polyesters, polypropylenes, polyethylenes, polyfluoroethylenes, silicone fluorinated polyolefins, fluorinated ethylene/propylene copolymer, perfluoroalkoxy fluorocarbon, ethylene/tetrafluoroethylene copolymer, and polyvinylpyrolidone. The bonding agent may constitute an interfacial layer between the scaffold and the substrate, or may be a polymeric cladding at least partially concentrically surrounding the scaffold. It should be noted that in embodiments in which the scaffold is adhered to the underlying substrate via an adhesive or bonding agent, the portions of the support members of the scaffold that are designed to translate with respect to other portions thereof when the prothesis is expanded from a collapsed configuration to an expanded configuration (e.g., disengaging portions of a first or second element) should have the ability to do so following the bonding process.

In another embodiment, a polymer may be applied to the scaffold, and a solvent applied over the scaffold to bond the scaffold to the substrate. A suitable solvent may be an aprotic solvent including dimethylacetamide (DMSE), dimethylformamide, THF, or their mixtures. For example, in one embodiment a generally tubular ePTFE substrate is positioned over a mandrel. The substrate may be sintered, unsintered, or partially sintered. Using a loading tool, a predetermined number of discrete expandable segments (or an elongate member forming spaced apart expandable segments) with a polyurethane coating are positioned along the outer surface of the ePTFE substrate. Depending on the material properties of the expandable segments, an additional crimping step may be required to secure the segments in position. Once the expandable segments are initially positioned on a surface of the substrate, a laser alignment fixture is optionally utilized to optimally space the adjacent expandable segments with respect to one another. The mandrel is then removed from the assembly and a solvent, such as tetrahydrofuran (THF), may be applied to the inside surface of the ePTFE substrate, so that the THF migrates through the wall of the ePTFE substrate. The interaction between the ePTFE, THF and polyurethane coating on the expandable segments bonds the segments to the ePTFE substrate (the THF or other aprotic solvent is believed to dissolve polyurethane, such that when a small amount contacts the polyurethane coating, a mechanical bond is developed between the coating and the ePTFE substrate).

In one embodiment, the expandable segments 110 are attached to the substrate 100 in an expanded configuration defining an expanded perimeter, the prothesis 10 and expandable segments 110 later being radially compressed to a collapsed configuration defining a collapsed perimeter of the expandable segments smaller than the expanded perimeter for delivery to a blood vessel. As shown in FIG. 1A and 1B, the expandable segments are discrete annular rings of connected struts. The expandable segments 112 include struts 124, 126, 128 arranged in an undulating configuration. Generally, the connected struts form a zig-zag pattern circumferentially around the prosthesis 10. The intersection of adjacent struts 124, 126 form an apex 120. Apexes aligned on the same side of the expandable section 112 form a first set of apexes. A second set of apexes 122, formed on the opposite side of the expandable section 112 by the intersection of different adjacent struts 124, 128, are offset from the first set of apexes 120. Preferably, the annular expandable segment is closed ended, which results in an equal number of apex in each set.

The lengths of the struts 124, 126, 128 may be uniform, as shown, or may be varied about the circumference of the expandable segment. For example, the expandable segment 112 could include two or more strut lengths arranged in patterns about its circumference. Many other expandable segment configurations are also possible and within the scope of the invention, such as, for example, sinusoidal patterns, meandering curve patterns, other zigzag patterns, or other curvilinear patterns. Any type of pattern or shape can be combined with other patterns or shapes to form non-uniform expandable segments. Moreover, it should be appreciated that the shape, size, thickness, material and/or other characteristic of the circumferential sections can be varied along the length of the prosthesis 10. Therefore, each expandable segment 112, 114, 116 need not be of the same material, shape, size, or configuration. Further, the undulations are not limited to zig-zag patterns but can be wave-like in form. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern.

In one embodiment, expandable segments 112, 114, 116 are positioned along a surface of the substrate 100 so that a first set of apex 122 of one expandable segment 112, aligns with the second set of apex 123 of an adjacent segment 114. The adjacent annular members 112 and 114 are spaced a sufficient distance apart to prevent interference between the segments upon radial compression or tortuous bending of the prosthesis 10. The expandable segments may be spaced at any sufficient distance to prevent interference and the spacing does not need to be uniform along the length of the prosthesis. Support members 150 extend generally transversely from the expandable segments 110 and are configured to engage and disengage as discussed above. Generally, the first and second elements are connected to adjacent expandable segments at a point near the adjacent segment. For example, for the zig-zag configuration of FIGS. 1A-1B, the first element 152 of support member 150 extends from the apex 122 of a first expandable segment 112, while the corresponding second element 154 extends from the apex 123 of the adjacent expandable segment 114. It should be noted that the support members do not need to be positioned on each apex of the expandable segment, nor do they need to be longitudinally aligned along the length of the prosthesis.

The first element of support member 150 can engage with the second element of support member 150 in various different ways. As shown in FIGS. 1A-1B, the first element 152 has two legs 156 and 158, while the second element 154 has a single leg 160. When the prosthesis 10 is in the collapsed configuration, at least the distal end of the legs 156, 158 contact at least the distal end of leg 160, the leg 156 contacting a surface of leg 160 generally opposite of the surface of leg 160 contacted by leg 158 such that the first element 152 is engaged with the second element 154. Upon expansion of the prosthesis 10 to an expanded configuration, the legs 156 and 158 of the first element 152 translate away from the leg 160 of the second element 154 such that the first element is disengaged from the second element 154. In one embodiment, a majority of the length of the leg 160 is contacted on either side by legs 156 and 158 such that the second element leg 160 is substantially between the first element legs 156, 158 in the collapsed configuration. In another embodiment, the first element and second element each include a single leg aligned and in contact when the prosthesis is in the collapsed configuration. The distal end of at least one of the first and second elements may include a detent or like feature in order to enhance the engagement contact therebetween in the collapsed configuration.

FIG. 1C and 1D illustrate other potential embodiments of the scaffold. In FIG. 1C, scaffold 130 is formed from individual, discrete, annular members. The annular members 132 and 134 are configured in a closed cell lattice formation. The annular members may be in a single closed cell lattice, 132, or multiple closed cell lattice, 134, or combinations thereof. The lattice is composed of connected struts 136, which may be generally straight, as shown, or curved, such that the closed cell 138 may assume several possible geometric shapes. Preferably, the annular members are cut from a tube of shape memory material (e.g., Nitinol). For example, longitudinal slits are laser cut into a solid Nitinol tube in such a manner as to form the desired closed cell configuration upon expansion of the tube. It should be appreciated that other methods of forming the annular members are possible and within the scope of the invention. For example, the single annular rings described above may be joined or connected together to form the single or plural closed cell lattice.

In FIG. 1D, the scaffold 140 includes one or more elongate members helically disposed about an outer surface of a substrate 100 from a first end of the prosthesis 10 to a second end. The distance between adjacent helical windings 142, 144 of elongate member 140 may be approximately equal along the length of the prosthesis 10, or may vary along the length. For example, beginning at one end of the prosthesis 10, the distance between the first two helical windings, 142 and 144, could be more or less than the distance between subsequent helical windings. The distance between adjacent helical windings could then progressively become greater or shorter along the length of the prosthesis, or could alternate between various distances. In embodiments including two or more elongate members, the members could be helically wound about the substrate in different directions and/or with different helical angles.

In one embodiment, the elongate member 140 includes struts 146 arranged generally in a zig-zag pattern, including a longer first strut and shorter adjacent strut that alternate along the length of the elongate member 140. The first, longer strut and second, shorter strut intersect at an apex 148. Adjacent pairs of struts will form two sets of apexes on alternate sides of the helical winding, which are offset from each other. The helical windings of an elongate member are positioned so that the first set of apexes on one helical winding is aligned with the second set of apexes from an adjacent helical winding. The adjacent windings are, additionally, spaced a sufficient distance apart to prevent interference between the windings upon radial compression or tortuous bending of the prosthesis. Therefore, the distance between adjacent helical windings is such that regardless of alignment, radial compression of the prosthesis will not result in interlocking the struts. Many other configurations are also possible for the elongate member 140 and are within the scope of the invention, such as, for example, sinusoidal patterns, meandering curve patterns, other zigzag patterns, or other curvilinear patterns. Any type of pattern or shape can be combined with other patterns or shapes to form non-uniform windings. Moreover, as discussed above, it should be appreciated that the shape, size, thickness, material and/or other characteristic of the elongate members can be varied along the length of the scaffold.

Figure 2A:
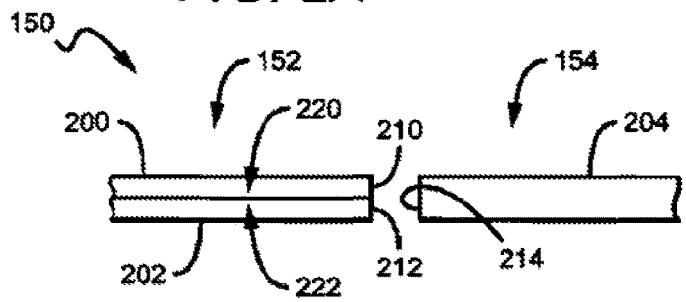
FIG. 2A is an enlarged view of a support member, including a first element and second element, when the prosthesis is in a collapsed configuration.
Figure 2B:
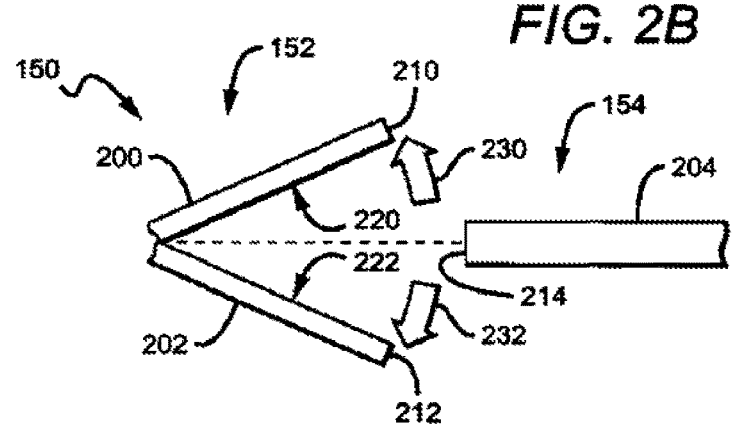
FIG. 2B is a view of the support member of FIG. 2A when the prosthesis is in an expanded configuration.

FIGS. 2A-2B illustrate support member 150, including first and second elements, 152 and 154, in the collapsed and expanded configuration. The first element 152 has two legs, 200 and 202, connected to the an expandable segment (not shown), while the second element 154 has a single leg 204 connected to an adjacent expandable section (not shown). Other embodiments include single legs for each of the first and second elements (FIGS. 3A-3C), two or more legs for each of the first and second elements where the number of legs for each is the same, and two or more legs for each of the first and second elements where the number of legs for each is different. As seen in FIG. 2A, when the support member 250 is in the collapsed configuration, the first and second elements 152, 154 generally align, and the distal portions, 220 and 222, of the legs 200 and 202 of the first element 152 are adjacent and substantially parallel. Both first and second elements, 152 and 154, are generally aligned with the longitudinal axis of the prosthesis. When the prosthesis is in the collapsed configuration, the distal ends of the first element 210, 212 are in contact with, or spaced a short distance from (e.g., less than about 100 microns), the distal end of the second element 214. In the case where slight spacing is present, the distal ends of the first element 210, 212 may come in contact with the distal ends of the second element 214 when the prosthesis is subject to compressive forces during deployment thereof (e.g., withdrawal of a delivery sheath from a constraining position over the prosthesis). When the prosthesis is expanded to the expanded configuration, the legs 200 and 202 of the first element 152 move in approximately opposite circumferential directions, as indicated by the arrows 230, 232 (FIG. 2B), such that the distal portions 220 and 222 of the legs 200 and 202 are spaced apart from each other and the distal ends 210, 212 of the legs 200 and 2002 are spaced apart from distal end 214 of the leg 204.

Figure 3A:
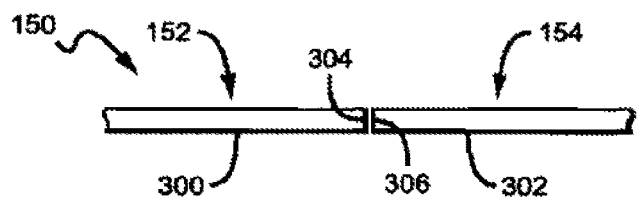
FIG. 3A is a view of another embodiment of a support member when the prosthesis is in a collapsed configuration.

In another embodiment, shown in FIG. 3A, the support member 150 has first and second elements 152 and 154, each of the first and second elements including a single leg 300 and 302 connected to adjacent expandable segments (not shown). Both legs 300 and 302 are generally aligned and parallel to the longitudinal axis of the prosthesis. When the support member 150 is in the collapsed configuration, the distal ends 304 and 306 of legs 300 and 302 are in contact with one another or spaced a short distance apart (e.g., less than about 100 microns). In the case where slight spacing is present, the distal ends 304 and 306 may come in contact when the prosthesis is subject to compressive forces during deployment thereof. Upon expansion of the prosthesis to the expanded configuration, the legs 300, 302 of the first and second elements 152, 154 disengage (e.g., are no longer in contact) through translation of one or both of the legs to a position that is no longer aligned with the longitudinal axis (i.e., the leg generally forms an oblique angle with respect thereto by translating in a circumferential direction).

Figure 3B:
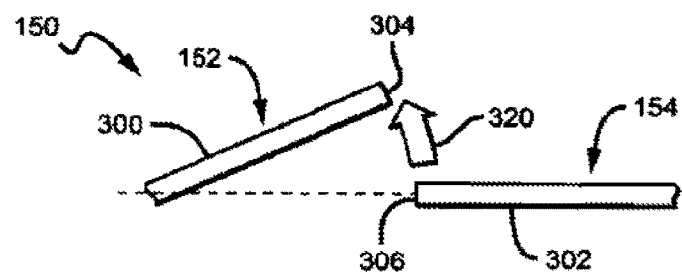
FIG. 3B is a view of one configuration of the support member of FIG. 3A when the prosthesis is in an expanded configuration.
Figure 3C:
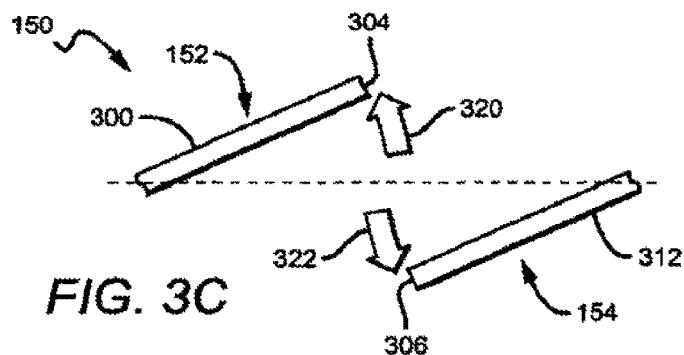
FIG. 3C is a view of another configuration of the support member of FIG. 3A when the prosthesis is in an expanded configuration.
Figure 3D:
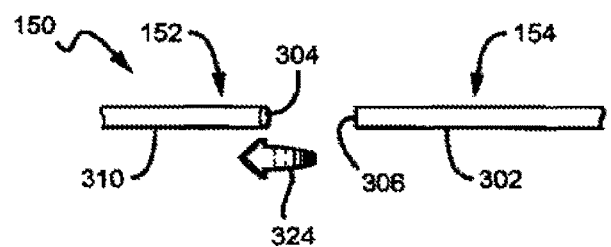
FIG. 3D is a view of yet another configuration of support member of FIG. 3A when the prosthesis is in an expanded configuration.

FIG. 3B shows the prosthesis in the expanded configuration, whereby leg 300 translates with respect to leg 302, which remains generally in the same position as in the collapsed configuration shown in FIG. 3A. FIG. 3C shows both legs 300, 302 translating to a position generally oblique to the longitudinal axis, the legs moving in different circumferential directions as indicated by arrows 320, 322. In another embodiment, the legs 300 and 302 are configured to move in the same general circumferential direction upon expansion of the prosthesis to an expanded configuration. In one embodiment, in addition to, or instead of, translating in a circumferential direction, one or more of the legs of the first and second elements will translate in a direction away from the central longitudinal axis of the prosthesis during expansion to the expanded configuration such that the distal ends of the legs may become embedded in a wall of the cavity or vessel into which the prosthesis is deployed. Thus, the legs may assist in preventing migration of the stent-graft, although it should be appreciated that the legs in most embodiments are sufficiently small to avoid complete penetration or perforation of the walls of the vessel. FIG. 3D shows one example of such an embodiment, in which leg 310 moves in the direction indicated by arrow 324, away from the central axis of the prosthesis when the prosthesis is expanded to an expanded configuration (i.e., distal end 304 moves out of the plane of the page toward the viewer).

Figure 4A:
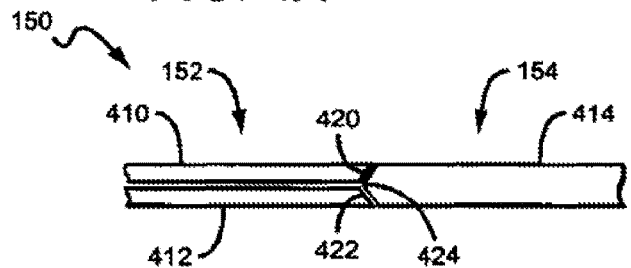
FIG. 4A is a view of one embodiment of a support member when the prosthesis is in a collapsed configuration.

FIG. 4A illustrates an embodiment of the first and second elements 152, 154, in which the distal ends 420, 422, and 424 of the legs thereof include complementary shapes. In the example shown, the distal ends 420 and 422 of the legs 410 and 412 are inwardly beveled in such a manner that when adjacent (i.e., when the prosthesis is in the collapsed configuration), they together form generally a "V" shape. Complementary, the distal end 424 of leg 414 includes a pointed configuration that extends into the "V" shape when the prosthesis is in the collapsed configuration. Complementary shapes for the distal ends of the first and/or second element of the support members therein may aid in preventing misalignment of the elements during loading and delivery of the prosthesis. Further, in one embodiment, a friction fit may be formed between the first element 152 and the second element 154 to further enhance the engagement. Other configurations are also possible and fall within the scope of the present invention. For example, the distal end of a first and second leg of the first element may form an inverted cone when collapsed and the distal end of the second element may form a complementary shape to extend into the inverted cone. Alternatively, the distal end of a first and second leg of the first element may have a cube edge or cylindrical indention to receive a complementary distal end of one or more legs of the second element.

Figure 4B:
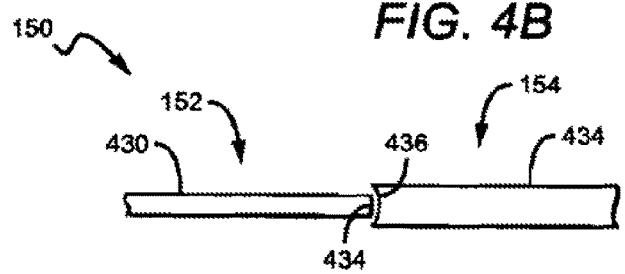
FIG. 4B is a view of another embodiment of a support member when the prosthesis is in a collapsed configuration.
Figure 4C:
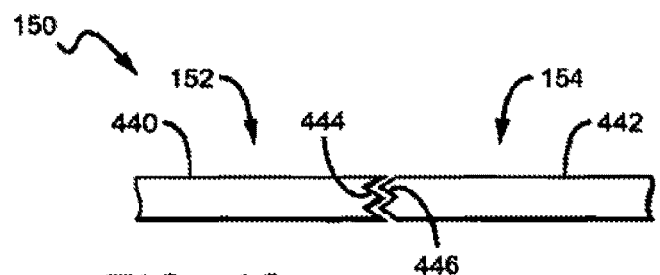
FIG. 4C is a view of yet another embodiment of a support member when the prosthesis is in a collapsed configuration.

FIGS. 4B-4C illustrate other configurations for the complementary shapes of the distal ends of the first and second elements 152, 154. In these example, different from the example in FIG. 2A, both the first element 152 and second element 154 include single legs with complementary shaped distal ends and the second element 154 distal end includes a detent-like feature while the first element 152 distal end includes a complementary-shaped protrusion. Of course, as with any of the embodiments described herein, the first and second elements may have distal end shapes that are reversed. FIG. 4B shows a "U" shaped detent on the distal end 436 of leg 432 of the second element 154, which is complemented by a rounded protrusion on the distal end 434 of leg 430 of the first element 152. FIG. 4C shows a "V" shaped detent on the distal end 446 of leg 442 of the second element 154 which is complemented by a "W" shaped protrusion on the distal end 444 of leg 440 of the first element 152. Of course, these examples should be considered non-limiting as other complementary shapes are also possible and within the scope of the invention.

Figure 5:
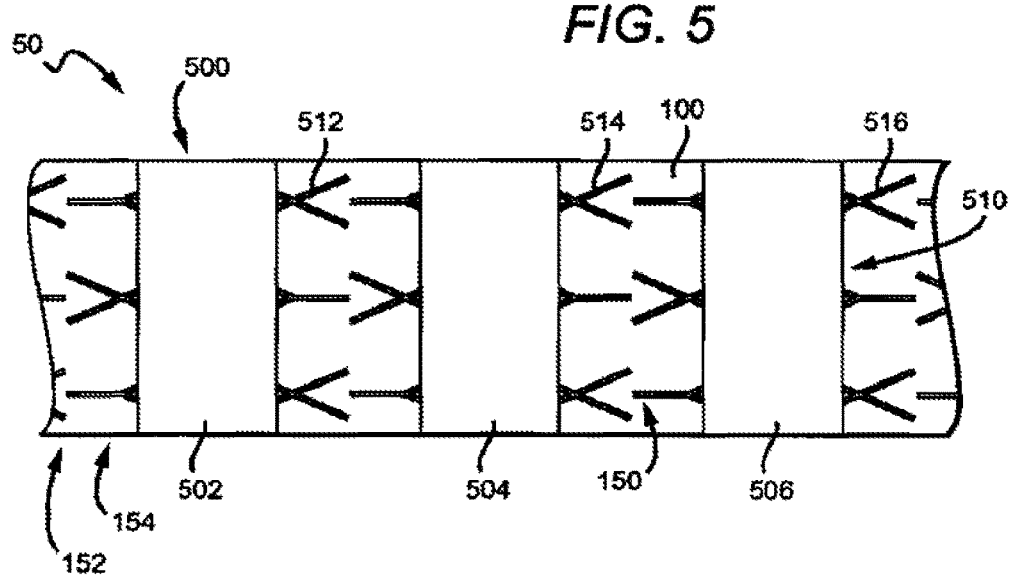
FIG. 5 is a partial side view of one embodiment of an implantable prosthesis including a scaffold with circumferential bands disposed about an outer surface.

FIG. 5 illustrates prosthesis 50 in its expanded configuration, featuring an optional outer layer 500. Outer layer 500 may provide additional support for the prosthesis 50 and/or a means for coupling the scaffold to the substrate in addition to, or instead of, other coupling methods, such as, for example, selective application of adhesives, application of a polymer to the annular members and bonding with a solvent, use of sutures to stitch the annular members to the substrate, etc. Outer layer 500 includes a plurality of circumferential bands, such as bands 502, 504, and 506, which are positioned over an outer surface of the expandable segments 512, 514, and 516, and are bonded to the substrate 100 at spaced apart locations. The bands are positioned such that support members 150 are substantially uncovered, including the first and second elements 152, 154, thereby permitting translation thereof when the prosthesis is expanded from the collapsed configuration to the expanded configuration and vice versa. In another embodiment, the substrate is positioned on an outer surface of the expandable segments 510, while the circumferential bands are positioned along an inner surface thereof.

The circumferential bands may be continuous, closed rings of material, or longitudinal strips of material with a first and second end that are circumferentially wrapped over the scaffold such that the first and second ends overlap. In other embodiments, longitudinal strips of material are used in combination with, or instead of, the circumferential bands. The longitudinal strips may be arranged over the scaffold outer surface such that it is aligned generally parallel to the longitudinal axis of the prosthesis or at an oblique angle therewith. One or more elongate strips of material may, in addition to or instead of the circumferential bands, be helically wound about the scaffold and substrate with a constant pitch or one that varies along the length of the prosthesis. The circumferential bands, longitudinal strip (s) and elongate strip(s) may include a material such as, for example, polytetrafluoroethylene, expanded polytetrafluoroethylene, fine metal meshes, linear polyethylene, polymers, combinations thereof, and/or any of the materials discussed above as potential materials for the substrate.

In a preferred embodiment, the outer layer 500 and substrate 100 are made of expanded polytetrafluoroethylene. In one embodiment, the outer layer 500 is brought into contact with the substrate through gaps in the expandable segment by applying inward pressure to the outside of the outer layer (e.g., by wrapping with tape), outward pressure to the inner surface of the substrate (e.g., by using a medical balloon), or both. The assembly is then subject to a heating process to bond the outer layer 500 to the substrate 100. For example, the assembly may be heated to a temperature above the melting point of the material from which the outer layer and substrate are formed so that the two materials flow together and remain interlocked upon cooling. Alternatively, the outer surface may be heated at discrete bonding locations to sinter the outer layer to the substrate at the bonding locations.

The prosthesis, as described herein, may be implanted into a patient to open and hold open a body lumen. One method of delivery of the prosthesis to a body lumen includes first placing the prosthesis into a delivery device. The prosthesis may be formed/assembled in the expanded configuration, meaning that it would first need to be collapsed into its collapsed configuration for insertion into the delivery device, or alternatively may be formed/assembled in a collapsed configuration. As discussed above, the elements of the support members are engaged in the collapsed configuration. The delivery device including the prosthesis is then introduced into a body lumen, for example, and deployed as known to one skilled in the art (e.g., by removal of a sheath whereby a self-expandable prosthesis expands in the absence of a constraining force, by balloon expanding the prosthesis, or some combination thereof). During deployment, the prosthesis is radially expanded to an expanded configuration, which expansion results in the decoupling or disengaging of the elements of the support members. Also, in some embodiments, one or more elements of the support members may become embedded in the vessel wall to prevent migration of the prosthesis. Following expansion of the prosthesis, the delivery device is removed from the patient.

Markers M1, M2, M3, M4 . . . Mn can be provided for all of the embodiments described herein. One or more markers may be positioned along the longitudinal axis of the prosthesis. The marker Mn can be formed from the same material as the stent as long as the material is radiographic or radiopaque. The marker material can also be formed, for example, from gold, tantalum, platinum, iridium, barium, sulfate, Nitinol, Hydroxyapatite, and combinations thereof. One or more markers can be formed from a marker material different from other markers.

The prosthesis described herein may be utilized with bio-active agents. Bio-active agents can be coated onto a portion or the entirety of the prosthesis, substrate, or circumferential bands for controlled release of the agents once the prosthesis is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus rapamyin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

This invention has been described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An implantable prosthesis having an expanded configuration (EC) with an expanded perimeter and a collapsed configuration (CC) with a collapsed perimeter smaller than the expanded perimeter comprising:
    a generally tubular substrate defining a longitudinal axis;
    a scaffold disposed over the substrate, the scaffold including:
        a series of longitudinally adjacent expandable rings, each of the expandable rings comprising a plurality of circumferentially adjacent struts joined together on one end at an apex to form a plurality of aligned apexes; and
        a gap defined between the plurality of aligned apexes of a first expandable ring and the plurality of aligned apexes of an adjacent expandable ring; and
    a plurality of support members, each support member including:
        a first element (FE) extending from the first expandable ring; and
        a second element (SE) extending from the adjacent expandable ring, wherein:
            the FE and the SE extend into the gap;
            the FE comprises a first FE leg and a second FE leg, inside lateral edges of the first FE leg and the second FE leg contact one another in the CC,
            the SE comprises an SE leg,
            in the CC, the first FE leg and the second FE leg are parallel to the longitudinal axis, each of the first FE leg and the second FE leg including an endpoint contacting an endpoint of the SE leg, and
            in the EC, the first FE leg and the second FE leg transition away from the SE leg in opposite directions to form oblique angles with respect to the longitudinal axis.

2. The implantable prosthesis of claim 1, wherein:
    the first FE leg and the second FE leg originate from a common apex,
    the endpoint of each of the first FE leg and the second FE leg together form a detent in the CC, and
    the endpoint of the SE leg includes a shaped surface configured to extend into and form a functional fit with the detent.

3. The implantable prosthesis of claim 2, further comprising a plurality of circumferential bands bonded to the substrate at spaced-apart locations, the bands positioned over an outer surface of the expandable rings such that a greater part of the scaffold is not covered.

4. The implantable prosthesis according to claim 3, wherein a configuration of the detent takes any one or any combination of the following shapes: "U" shaped, "V" shaped, and "W" shaped.

5. The implantable prosthesis according to claim 2, wherein the detent forms a "V" shape.

6. The implantable prosthesis according to claim 5, wherein the endpoint of the SE leg is configured to extend into the "V" shape.

7. The implantable prosthesis according to claim 1, wherein in the EC the SE leg is parallel to the longitudinal axis.

8. The implantable prosthesis according to claim 1, wherein the first FE leg and the second FE leg originate from a common apex.

9. An implantable prosthesis having an expanded configuration (EC) with an expanded perimeter and a collapsed configuration (CC) with a collapsed perimeter smaller than the expanded perimeter comprising:
    a generally tubular substrate defining a longitudinal axis;
    a scaffold disposed over the substrate, the scaffold including:
        a series of longitudinally adjacent expandable rings, each of the expandable rings comprising a plurality of circumferentially adjacent struts joined together on one end at an apex to form a plurality of aligned apexes; and
        a gap defined between the plurality of aligned apexes of a first expandable ring and the plurality of aligned apexes of an adjacent expandable ring; and a plurality of support members, each support member including:
a first element (FE) extending from the first expandable ring; and
a second element (SE) extending from the adjacent expandable ring,
wherein:
the FE and the SE extend into the gap;
the FE comprises a first FE leg and a second FE leg,
the first FE leg and the second FE leg originate from a common apex,
inside lateral edges of the first FE leg and the second FE leg contact one another in the CC,
the SE comprises an SE leg,
in the CC, the first FE leg and the second FE leg are parallel to the longitudinal axis, each of the first FE leg and the second FE leg including an endpoint contacting an endpoint of the SE leg,
the endpoint of each of the first FE leg and the second FE leg together form a detent in the CC,
the endpoint of the SE leg includes a shaped surface configured to extend into and form a functional fit with the detent, and
in the EC, the first FE leg and the second FE leg transition away from the SE leg in opposite directions to form oblique angles with respect to the longitudinal axis.

10. The implantable prosthesis of claim 9, further comprising a plurality of circumferential bands bonded to the substrate at spaced-apart locations, the bands positioned over an outer surface of the expandable rings such that a greater part of the scaffold is not covered.

11. The implantable prosthesis according to claim 10, wherein a configuration of the detent takes any one or any combination of the following shapes: "U" shaped, "V" shaped, and "W" shaped.

12. The implantable prosthesis according to claim 9, wherein the detent forms a "V" shape.

13. The implantable prosthesis according to claim 12, wherein the endpoint of the SE leg is configured to extend into the "V" shape.

* * * * *